(12) United States Patent
Wu et al.

(10) Patent No.: US 12,186,913 B2
(45) Date of Patent: Jan. 7, 2025

(54) AUTOMATED COLLISION AVOIDANCE IN MEDICAL ENVIRONMENTS

(71) Applicant: Shanghai United Imaging Intelligence Co., LTD., Shanghai (CN)

(72) Inventors: Ziyan Wu, Cambridge, MA (US); Srikrishna Karanam, Cambridge, MA (US); Meng Zheng, Cambridge, MA (US); Abhishek Sharma, Cambridge, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 377 days.

(21) Appl. No.: 17/564,919

(22) Filed: Dec. 29, 2021

(65) Prior Publication Data
US 2023/0202044 A1 Jun. 29, 2023

(51) Int. Cl.
| | | |
|---|---|---|
| G06V 20/52 | (2022.01) | |
| A61B 5/055 | (2006.01) | |
| A61B 6/03 | (2006.01) | |
| A61B 6/10 | (2006.01) | |
| A61B 34/30 | (2016.01) | |
| B25J 9/16 | (2006.01) | |
| B25J 13/08 | (2006.01) | |
| G05D 1/00 | (2006.01) | |
| G06T 7/215 | (2017.01) | |
| G06T 7/254 | (2017.01) | |
| G06T 19/00 | (2011.01) | |
| G06V 10/25 | (2022.01) | |

(Continued)

(52) U.S. Cl.
CPC .............. *B25J 9/1676* (2013.01); *A61B 6/102* (2013.01); *B25J 13/08* (2013.01); *G05D 1/0253* (2013.01); *G06T 7/215* (2017.01); *G06V 10/768* (2022.01); *G06V 20/64* (2022.01)

(58) Field of Classification Search
CPC . B25J 9/1676; B25J 13/08; B25J 9/163; B25J 9/1666; B25J 9/1697; B25J 9/00; B25J 9/16; B25J 9/1674; B25J 19/021; A61B 6/102; A61B 5/055; A61B 6/035; A61B 6/44; A61B 34/30; G05D 1/0253; G06T 7/215; G06T 7/254; G06T 7/248; G06T 19/003; G06T 2207/10016; G06T 2207/10028; G06T 2207/10081; G06T 2207/10088; G06V 10/768; G06V 20/64; G06V 20/52; G06V 10/25; G05B 2219/39082; G05B 2219/40317; G05B 19/4061; G05B 10/4061; A61N 2005/1092

See application file for complete search history.

(56) References Cited

U.S. PATENT DOCUMENTS

| | | | | |
|---|---|---|---|---|
| 11,016,491 | B1 * | 5/2021 | Millard | G06N 3/045 |
| 11,422,546 | B2 * | 8/2022 | Giering | G06F 18/251 |
| 11,478,942 | B1 * | 10/2022 | Lee | B25J 18/025 |

(Continued)

*Primary Examiner* — Adam R Mott
*Assistant Examiner* — Byron Xavier Kasper
(74) *Attorney, Agent, or Firm* — Zhong Law, LLC (57) ABSTRACT

An apparatus for automated collision avoidance includes a sensor configured to detect an object of interest, predicting a representation of the object of interest at a future point in time, calculating an indication of a possibility of a collision with the object of interest based on the representation of the object of interest at the future point in time, and executing a collision avoidance action based on the indication.

18 Claims, 3 Drawing Sheets

(51) Int. Cl.
    *G06V 10/70*        (2022.01)
    *G06V 20/64*        (2022.01)

(56)            References Cited

U.S. PATENT DOCUMENTS

| | | | |
|---|---|---|---|
| 11,797,022 B1* | 10/2023 | Ballantyne | G06T 7/13 |
| 2017/0220709 A1* | 8/2017 | Wan | A61N 5/1048 |
| 2018/0141213 A1* | 5/2018 | Tsao | B25J 9/1676 |
| 2021/0097852 A1* | 4/2021 | Yoo | G08G 1/005 |
| 2022/0066456 A1* | 3/2022 | Ebrahimi Afrouzi | G06F 3/04883 |
| 2022/0148119 A1* | 5/2022 | Yokota | G06V 10/26 |
| 2022/0160445 A1* | 5/2022 | Meglan | B25J 9/1676 |
| 2022/0366594 A1* | 11/2022 | Meglan | A61B 1/00193 |
| 2023/0113312 A1* | 4/2023 | Junio | A61B 34/70 700/255 |

\* cited by examiner

AUTOMATED COLLISION AVOIDANCE IN MEDICAL ENVIRONMENTS

FIELD

The aspects of the disclosed embodiments relate generally to object detection, and more particularly to automated collision prediction and avoidance in a medical environment.

BACKGROUND

Existing systems in medical environments may rely on ultrasonic and contact sensors to detect collisions. Ultrasonic sensors are usually mounted on moving parts of devices such as robotic arms and can detect objects within a relatively close range. When an object gets within a predetermined range the device can stop its movement. A drawback of ultrasonic sensors is the limited field of view, which provides coverage for a very small region.

Similar to ultrasonic sensors, contact sensors are usually mounted on the moving part of the device. Contact sensors rely on the detection of physical contact with the object to prevent severe collisions. Such contact sensors tend to have an even smaller coverage area and are typically used as a last layer of protection, after a collision has already occurred. These approaches do not provide a sufficient amount of collision avoidance, and do not provide a required degree of safety assurance to personnel in the medical environment.

Accordingly, it would be desirable to provide methods and apparatus that address at least some of the problems described above.

SUMMARY

The aspects of the disclosed embodiments are directed to automated collision avoidance in the medical environment. This and other advantages of the disclosed embodiments are provided substantially as shown in, and/or described in connection with at least one of the figures, as set forth in the independent claims. Further advantageous modifications can be found in the dependent claims.

According to a first aspect, the disclosed embodiments are directed to an apparatus for automated collision avoidance in a medical environment. In one embodiment the apparatus includes a sensor or sensors configured to detect at least one object of interest in a space; predict a representation of the object of interest in the space at a future point in time; calculate an indication of a possibility of a collision of the object of interest with another object in the space based on the representation of the object of interest at the future point in time, and execute a collision avoidance action based on the indication.

In a possible implementation form, the apparatus is mounted on or disposed in connection with a robotic system configured to move in a medical environment.

In a possible implementation form the apparatus includes more than one sensor or a sensor array.

In a possible implementation form of the apparatus, the sensor is a visual sensor.

In a possible implementation form, the sensor includes one or more cameras.

In a possible implementation form of the apparatus, the sensor is one or more of an RGB sensor, a depth sensor or an infrared sensor.

In a possible implementation form, the apparatus includes one or more of a stationary sensor or a mobile sensor.

In a possible implementation form, the representation of the object of interest can be one or more of a 3D point cloud, a mesh representation or a voxel representation.

In a possible implementation form the apparatus is configured to predict the representation of the object of interest at a future point of time based on current motion information of the object of interest that is estimated based on representations of one or more of a current state of the object of interest or a previous state.

In a possible implementation form the motion information is one or more of a 2D velocity, a 3D velocity or an acceleration of the object of interest.

In a possible implementation form the calculated indications are projections of the representation of the object of interest, and a part of the robotic system, onto different 2D planes (e.g., x-y plane, x-z plane and y-z plane) respectively.

In a possible implementation form the processor is configured to evaluate the projections and determine the likelihood of a collision between a part of the robotic system and the object of interest within a pre-determined time window, based on a pre-determined or learned metric, such as a union of intersection between the part of robotic system and the object of interest on each projection plane.

In a possible implementation form, the apparatus is configured to compare an image of the space acquired at a time $t_n$ to an image of the space acquired at a time $t_{n-1}$; calculate a movement of one or more pixels between the different images and calculate the possibility of the collision based on the pixel movement.

In a possible implementation form, the apparatus is configured to capture images of the space at different times in a continuous manner, compare the different images to determine movement of pixels between the different images and calculate the possibility of collision based on the pixel movement.

In a possible implementation form the apparatus is configured to estimate a moving direction and a velocity for each pixel or point in and between the different images of the space.

In a possible implementation form the apparatus is configured to predict a next position for a pixel or point in the space.

In a possible implementation form, the apparatus is integrated with an Angiography suite. The motion trajectory of the c-arm of the Angio suite is pre-calculated and evaluated by the processor, together with the predicted representations of the patient, patient support and other equipment and persons in the Angio suite in a future point of time within the window of the trajectory arriving at a consolidated decision such as whether the c-arm should proceed with the motion, re-plan the trajectory, stop the motion, or request manual intervention.

In a possible implementation form the apparatus is integrated with a radiation therapy system. The apparatus is configured to prevent the rotating treatment head from colliding with the patient, the patient support or other equipment.

In a possible implementation form, the apparatus is integrated with a surgical robotic system. The apparatus is configured to provide support and feedback on the trajectory planning of the robotic arms, as well as safety assurance to the patient, medical personnel, as well as equipment, throughout the operation.

In a possible implementation form, the apparatus is integrated with a medical scanner such as a computed tomography (CT) or magnetic resonance (MR) scanner. The apparatus is configured to provide prediction and warnings when there is an indication that the patient may be or is colliding with the scanner or other equipment in the scanning room.

In a possible implementation form, the apparatus is integrated with an x-ray system. The x-ray system can be either ceiling mounted or floor mounted. The apparatus is configured to predict and prevent collisions between a patient and a part of the x-ray system (e.g., robotic arms, the x-ray tube or the flat panel) during the scanning or positioning process. The apparatus is configured to guide the x-ray robotic arms during navigation and path planning process to avoid obstacles.

According to a second aspect, the disclosed embodiments are directed to a method. In one embodiment, the method includes detecting an object of interest; predicting a representation of the object of interest at a future point in time; calculating an indication of a possibility of a collision with the object of interest based on the representation of the object of interest at the future point in time, and executing a collision avoidance action based on the indication.

In a possible implementation form the method includes predicting the representation of the object of interest at a future point of time based on current motion information of the object of interest that is estimated based on representations of one or more of a current state of the object of interest or a previous state.

In a possible implementation form, the method includes calculating the indications by projecting representations of the object of interest, and a part of the equipment or robotic system, onto different 2D planes, respectively.

According to a third aspect, the disclosed embodiments are directed to a computer program product embodied on a non-transitory computer readable medium, the computer program product comprising computer instructions that, when executed on at least one processor of a system or an apparatus, is configured to perform the possible implementation forms described herein.

According to a fourth aspect, the disclosed embodiments are directed to a device comprising means for performing the possible implementation forms described herein.

These and other aspects, implementation forms, and advantages of the exemplary embodiments will become apparent from the embodiments described herein considered in conjunction with the accompanying drawings. It is to be understood, however, that the description and drawings are designed solely for purposes of illustration and not as a definition of the limits of the disclosed invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

In the following detailed portion of the present disclosure, the invention will be explained in more detail with reference to the example embodiments shown in the drawings, in which.

DETAILED DESCRIPTION OF THE DISCLOSED EMBODIMENTS

The following detailed description illustrates exemplary aspects of the disclosed embodiments and ways in which they can be implemented. Although some modes of carrying out the aspects of the disclosed embodiments have been disclosed, those skilled in the art would recognize that other embodiments for carrying out or practising the aspects of the disclosed embodiments are also possible.

Figure 1:
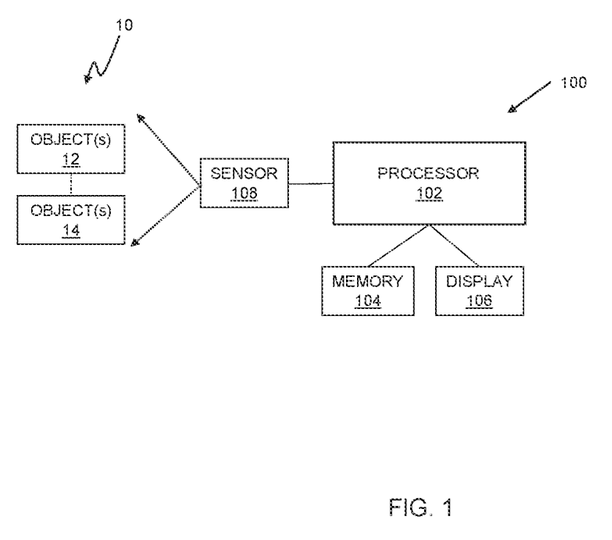
FIG. 1 is a block diagram of an apparatus incorporating aspects of the disclosed embodiments.

Referring to FIG. 1, a schematic block diagram of an exemplary apparatus 100 incorporating aspects of the disclosed embodiments is illustrated. The aspects of the disclosed embodiments are generally directed to automated collision avoidance in a medical environment. The apparatus 100 is configured detect a potential collision between different object 12 and at least on other object 14, in a space or environment 10, such as a room. For purposes of the description herein, the environment will be referred to as a "space."

The object 12, and at least one other object 14, also referred to as object(s) of interest, can include one or more of equipment or people. The aspects of the disclosed embodiments are configured to avoid collisions between different pieces of equipment, as well as equipment and people, particularly in a medical environment. The apparatus 100 will advantageously lower the risk of damage to equipment and injury to people in an environment, such as a medical environment.

Although the aspects of the disclosed embodiments will be described herein with respect to collisions between object 12 and at least one other object 14, the aspects of the disclosed embodiments are not so limited. For example, one of the objects 12, 14 could be a wall or other structure of the environment 10. In this embodiment, the apparatus 100 can be configured to predict such a collision.

For the purposes of the disclosure herein, the aspects of the disclosed embodiment will generally be described with respect to object 12. In alternate embodiments, the aspects of the disclosed embodiments as described herein can equally apply to the at least one object 14.

Referring to FIG. 1, the apparatus 100 generally comprises a sensor 108 that is communicatively connected or coupled to a processor 102. The sensor 108 is generally configured to detect or capture images of one or more objects 12, 14 that are within a field of view of the sensor 108. In one embodiment, the sensor(s) 108 is configured to capture images of the space 10. Although only one sensor 108 is generally referred to herein, the aspects of the disclosed embodiments are not so limited. In alternate embodiments the apparatus 100 can include any suitable number of sensors 108, other than including one. In one embodiment, the sensor 108 can comprise an array of sensors 108. The sensors 108 in such an array can be communicatively coupled together, or a sensor 108 can be configured to communicate with the processor 102 as is generally described herein.

In the example of FIG. 1, the processor 102 is configured to predict a representation of the object of interest in the space at a future point of time based on the detection of the object 12 or the images captured by the sensor 108. Using the predicted representation, the processor 102 is configured to calculate an indication of a possibility of a collision of the object 12 with the at least one other object 14 in the space 10 and execute a collision avoidance action based on the indication. The aspects of the disclosed embodiments advantageously use visual sensors to automatically predict and detect collisions between different objects in an environment, such as equipment and people.

In one embodiment, the sensor 108 comprises an image or imaging sensor, such as a visual sensor. In alternate embodiments, the sensor 108 can comprises any suitable type of visual sensor, such as a camera, for example. Other examples of the sensor 108 can include, but are not limited to, a red-green-blue (RGB) sensor, a depth sensor or an infrared sensor. The sensor 108 can also be a stationary sensor or a mobile sensor, or a combination thereof.

In one embodiment, the sensor 108 can be remotely located from the apparatus 100. For example, if the apparatus 100 is disposed in a room, the sensor 108 could be disposed in the room away from the apparatus 100. In this manner, the sensor 108, or one or more sensor(s) 108, can be uniquely positioned or disposed to provide accurate information with respect to different objects of interest 10 within the room. In this example, the sensor(s) 108 and the processor 102 can be communicatively coupled by a suitable communication network.

The processor 102 is generally configured to detect one or more of the objects 12, 14 based on the image data provided by the sensor(s) 108. Any suitable image detection algorithm can be used to detect objects in an image.

In one embodiment, the apparatus 102 is configured to predict a representation of the object 12 in the space 10 at a future point in time based on the image data provided by the sensor 108. In this manner, the processor 102 is configured to identify, or predict, where, for example, object 12 will be positioned relative to the at least one other object 14 in the space 10 at a later point in time, or time point, in order to predict the possibility of collision of objects 12 and 14.

In one embodiment, the prediction of the representation of the object 12 at a future point of time is based on current motion information of the object 12. For example, the sensor 108 is configured to gather motion information corresponding to object 12. This can include for example, capturing a series of images of the object 12, or the space 10 in which the object 12 is disposed. As noted above, the prediction described herein can be equally applied to the at least one other object 14.

For example, in one embodiment where the sensor 108 is a camera, the camera can capture images of the space 10 or object 12 at different time points $t_{(n)}$. The processor 102 can be configured to compare an image or images captured at time point $t_{(n)}$ with an image captured at time point $t_{(n-1)}$. The differences in the different images can be used to predict the representation of the object 12 at a next time point $t_{(n-1)}$.

In one embodiment, the processor 102 is configured to determine or calculate pixel movement between the image at time point $t_{(n)}$ and the image at time point $t_{(n-1)}$. By identifying or calculating the movement of pixels from one image to a next image, the processor 102 can determine or identify the movement of the object 12, or any other object 14, in the image, as well as a magnitude of such movement(s). In one embodiment, an optical flow algorithm can be used to calculate pixel movements between different images or different timespans. By doing this for consecutive time steps $T_{(n)}$, $T_{(n-1)}$, the moving direction and velocity of each point or pixel in the image of the space 10 can be estimated. In this manner, a prediction can be made as to where each point or pixel in the space is going to be in a next time step $T_{(n+1)}$. A determination of any collision between different objects 12, 14 in the space 10 can then be made based on the prediction.

In one embodiment, the processor 102 is configured to determine motion information associated with the object 12. This motion information can include for example, a two-dimensional (2D) or three dimensional (3D) velocity of the object 12, as well as an acceleration of the object 12. In one embodiment, the motion information can be estimated based on representations of one or more of a current state or a previous state of the object 12. It will be understood that the sensor(s) 108 are continually detecting and updating information on the object(s) of interest 12 in the environment.

The processor 102 is configured to use the information from the sensor 108 to predict a collision between the object 12 and at least one other object 14, as well as initiate collision avoidance actions.

In one embodiment, the processor 102 is configured to extract a representation of the object 12 from the information captured by the sensor(s) 108. The representation can comprise for example a three-dimensional (3D) cloud representation, a mesh or a voxel representation. In alternate embodiments, the representation can be any suitable representation that enables the processor 102 to identify characteristics of the object 12. These characteristics can include, but are not limited to, a geometric shape of the object 12, a movement or motion of the object 12, a direction, acceleration, velocity and speed of such movement and a relative position of the object 12 with respect to at least one other object. In alternate embodiments, the characteristics can include any suitable characteristics that can be used to predict a collision between the object 12 and at least one other object.

In one embodiment, the processor 102 is configured to calculate and determine one or more indications which can be used to gauge the possibility of a collision between the object 12 and another object such as object 14, at a given point of time, based on the predicted representation of the object 12. The calculated indications can be projections of the representation of the object 12 and at least a part of another object 14, onto different two-dimensional (2D) planes. The 2D planes can include for example the x-y plane, x-z plane and y-z plane.

In one embodiment, the processor 102 is configured to evaluate the different projections of the representation of the object 12 and the at least one other object 14, and determine a likelihood of a collision. In one embodiment, the likelihood of collision between a part of the object 12 and a part of the at least one other object 14 can be determined within a pre-determined time window.

The likelihood of collision can be determined based on a pre-determined or learned metric. This learned metric can include for example, but is not limited to a union of intersection between at least part of the object 12 and at least part of the at least one other object 14 on or for each of the different projection planes.

Once the likelihood of collision is evaluated or predicted, the processor 102 is configured to initiate or execute responsive actions. Such responsive actions can include, but are not limited to, stopping movement of the objects 12 or 14, changing or adjusting a movement, initiating an alarm or warning for example. In alternate embodiments, any suitable collision avoidance acts or actions can be taken or initiated.

Figure 2:
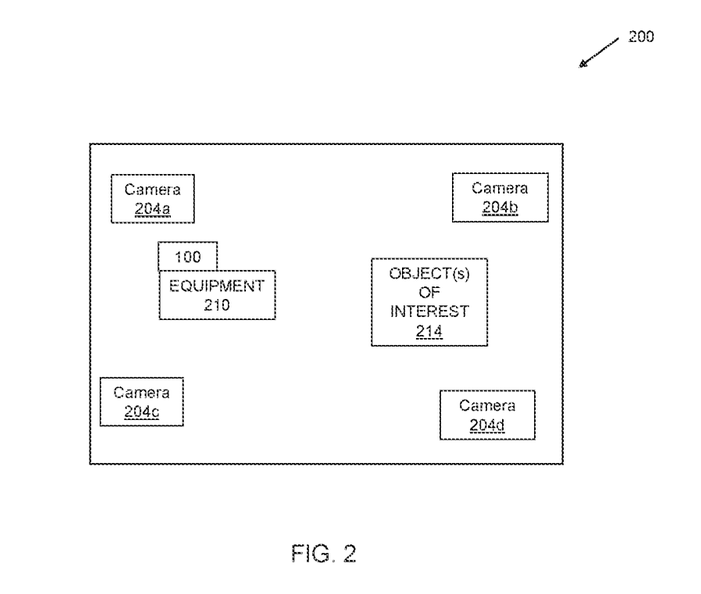
FIG. 2 is a block diagram of an exemplary environment for an apparatus incorporating aspects of the disclosed embodiments.

Referring to FIG. 2, the apparatus 100 is configured to be disposed or implemented in an environment 200, such as a medical environment or medical imaging environment. In this example, the apparatus 100 is disposed on or in connection with a medical imaging device or equipment 210. Alternatively, the apparatus 100 can be a standalone device.

In one embodiment, the apparatus 100 can also be communicatively coupled to the medical device 210. Examples of such medical systems can include, but are not limited to, x-ray systems, medical resonance imaging (MRI) systems, computed tomography (CT) systems, and surgical robotic systems. In alternative embodiments, the apparatus 100 can be embodied in or part of any suitable device or system where collision avoidance is desired.

In one embodiment, the device 210 is, includes or is connected to a robotic device or system. The aspects of the disclosed embodiments can be implemented in conjunction with systems or devices that are configured to move or rotate.

In the example of FIG. 2, the sensors 108 comprise the cameras 204a-204d. The cameras 204a-204d are configured to communicate with the apparatus 100 in this example. As is described herein, the cameras 204a-204d are used to detect the object 214 relative to the equipment 210. A representation of the object 214 and/or the equipment at a next or future point of can be predicted and used to determine a possibility of a collision between the equipment 210 and the object of interest 214, as is generally described.

Figure 3:
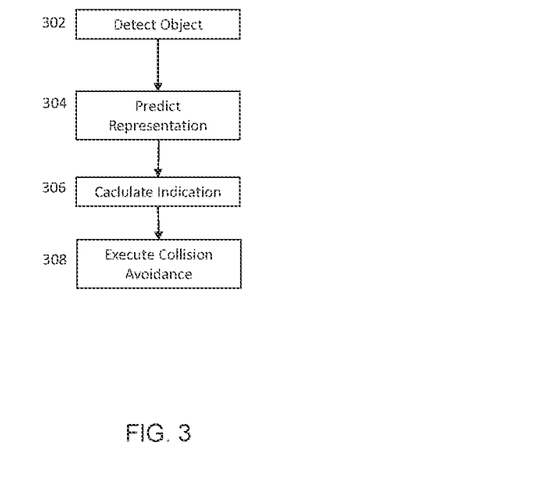
FIG. 3 is a flowchart illustrating an exemplary process flow incorporating aspects of the disclosed embodiments.

FIG. 3 is a flowchart illustrating an exemplary method incorporating aspects of the disclosed embodiments. In this example, the method includes detecting 302 an object of interest in the environment. A representation of the object of interest at a next or future point of time is predicted 304. In one embodiment, the prediction the representation of the object of interest at a future point of time is based on current motion information of the object of interest that is estimated based on representations of one or more of a current state of the object of interest or a previous state.

An indication of a possibility of a collision of an apparatus with the object of interest based on the representation of the object of interest at the future point in time is calculated 306. In one embodiment calculating the indications includes projecting representations of the object of interest, and a part of the equipment onto different 2D planes, respectively. A collision avoidance action based on the indication is executed 308.

The apparatus 100 can be disposed or implemented in many different environments 12. An exemplary system 200 incorporating aspects of the disclosed embodiments is shown in FIG. 2. For example, in one embodiment, the apparatus 100 is integrated with an equipment 10, such as an Angio suite. The motion trajectory of the c-arm of the Angio suite is pre-calculated and evaluated by the processor 102, together with the predicted representations of the patient, patient support and other equipment and persons in the suite at a future point of time. The predicted representations can be made within a window of the trajectory of the c-arm. The processor 102 in this example can be configured to determine whether the c-arm should proceed with the motion, re-plan the trajectory, stop the motion, or request manual intervention.

In an embodiment, the apparatus 100 is integrated with a radiation therapy system. The apparatus 100 in this example is configured to prevent the rotating treatment head from colliding with the patient, the patient support or other equipment.

In an embodiment, the apparatus 100 is integrated with a surgical robotic system. The apparatus 100 is configured to provide support and feedback on the trajectory planning of the robotic arms of the system. The apparatus 100 can also provide safety assurance for the patient, medical personnel, as well as the associated equipment, throughout the operation.

In an embodiment, the apparatus 100 is integrated with a medical scanner such as CT or MR. In this example, the apparatus 100 is configured to provide prediction and warnings when there is an indication of a collision between the patient and the scanner or other equipment in the scanning room.

In an embodiment, the apparatus 100 is integrated with an x-ray system. The x-ray system can be either ceiling mounted or floor mounted. The apparatus 100 is configured to predict and prevent collisions between, for example, a patient and a part of the x-ray system. This can include the robotic arms, the x-ray tube or the flat panel, for example, during the scanning or positioning process. The apparatus 100 is also configured to guide the x-ray robotic arms during navigation and path planning process to avoid obstacles.

In one embodiment, the apparatus 100 shown in FIG. 1, generally comprises a computing device. The computing device can comprise or include any suitable computer or computing arrangement.

In one embodiment, the processor 102 comprises a hardware processor. Although only one processor 102 is generally described herein, the aspects of the disclosed embodiments are not so limited. In alternate embodiments, the apparatus 100 can include any suitable number of processors 102.

The apparatus 100 generally includes suitable logic, circuitry, interfaces and/or code that is configured to receive the information from the sensor(s) 108 and process the information as is generally described herein.

The processor 102 generally includes suitable logic, circuitry, interfaces and/or code that is configured to process the information and data as is generally described herein. The processor 102 is configured to respond to and process instructions that drive the apparatus 100. Examples of the processor 102 include, but are not limited to, a microprocessor, a microcontroller, a complex instruction set computing (CISC) microprocessor, a reduced instruction set (RISC) microprocessor, a very long instruction word (VLIW) microprocessor, or any other type of processing circuit. Optionally, the processor 102 may be one or more individual processors, processing devices and various elements associated with a processing device that may be shared by other processing devices. Additionally, the one or more individual processors, processing devices and elements are arranged in various architectures for responding to and processing the instructions that drive the system 100. The apparatus 100 can include any suitable components or devices that are needed to carry out the processes described herein, such as a memory or storage, for example.

In one embodiment, the apparatus 100 can comprise or be part of a standalone computing device, in communication with, or part of, the equipment 10. In one embodiment, the apparatus 100 will include or be connected to the machine learning models needed to carry out the aspects of the disclosed embodiments described herein.

In the example of FIG. 1, the apparatus 100 also includes or is communicatively coupled to a memory 104. Although not shown, the apparatus 100 could be communicatively coupled to network or network interface to enable communication with the components and devices of the apparatus 100.

The memory 104 may comprise suitable logic, circuitry, interfaces, and/or code that may be configured to store instructions executable by the processor 102. The memory 104 is further configured to store the sensor information, state information and predictions. The memory 104 may be further configured to store operating systems and associated applications of the processor 102. Examples of implementation of the memory 104 may include, but are not limited to, Random Access Memory (RAM), Read Only Memory (ROM), Hard Disk Drive (HDD), Flash memory, and/or a Secure Digital (SD) card. A computer readable storage medium of a computer program product for providing a non-transient memory may include, but is not limited to, an electronic storage device, a magnetic storage device, an optical storage device, an electromagnetic storage device, a semiconductor storage device, or any suitable combination of the foregoing.

The aspects of the disclosed embodiments are directed to collision avoidance in an environment, such as a medical environment. Visual sensors are used to provide large enough coverage and early detection of potential collision to further lower the risk of damage to persons and devices in the medical environment.

Various embodiments and variants disclosed above, with respect to the aforementioned system 100, apply mutatis mutandis to the method. The method described herein is computationally efficient and does not cause processing burden on the processor 102.

Modifications to embodiments of the aspects of the disclosed embodiments described in the foregoing are possible without departing from the scope of the aspects of the disclosed embodiments as defined by the accompanying claims. Expressions such as "including", "comprising", "incorporating", "have", "is" used to describe and claim the aspects of the disclosed embodiments are intended to be construed in a non-exclusive manner, namely allowing for items, components or elements not explicitly described also to be present. Reference to the singular is also to be construed to relate to the plural.

Thus, while there have been shown, described and pointed out, fundamental novel features of the invention as applied to the exemplary embodiments thereof, it will be understood that various omissions, substitutions and changes in the form and details of devices and methods illustrated, and in their operation, may be made by those skilled in the art without departing from the spirit and scope of the presently disclosed invention. Further, it is expressly intended that all combinations of those elements, which perform substantially the same function in substantially the same way to achieve the same results, are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. An apparatus for automated collision avoidance in a medical environment, the apparatus comprising a processor configured to:
    detect, in the medical environment, a potential obstacle to a medical device based on image data of the medical environment captured by a sensor;
    predict a three-dimensional (3D) representation of the potential obstacle in the medical environment at a future point in time, wherein the 3D representation comprises a 3D point cloud, a 3D mesh or a voxel, and wherein the processor is further configured to determine motion information of the potential obstacle based on a first image of the medical environment and a second image of the medical environment captured by the sensor, the processor further configured to predict the 3D representation of the potential obstacle at the future point in time based at least on the determined motion information;
    predict a 3D representation of the medical device at the future point in time;
    project the predicted 3D representation of the potential obstacle and the predicted 3D representation of the medical device onto at least one two-dimensional (2D) projection plane;
    determine a possibility of a collision between the potential obstacle and the medical device based on the projection; and
    execute a collision avoidance action based on the determined possibility of the collision.

2. The apparatus according to claim 1, wherein the determined motion information of the potential obstacle includes a moving direction and a moving speed of the potential obstacle.

3. The apparatus according to claim 2, wherein the processor being configured to determine the motion information of the potential obstacle comprises the processor being configured to determine a current state of the potential obstacle based on the first image captured by the sensor, determine a previous state of the potential obstacle based on the second image captured by the sensor, and determine the motion information of the potential obstacle based on the current state and the previous state of the potential obstacle.

4. The apparatus according to claim 1, wherein the predicted 3D representation of the potential obstacle and the predicted 3D representation of the medical device are project onto multiple 2D projection planes, and wherein
    the possibility of the collision between the potential obstacle and the medical device is determined based on a union of intersection between respective projections of the predicted 3D representation of the potential obstacle and the predicted 3D representation of the medical device on each of the multiple 2D projection planes.

5. The apparatus according to claim 1, wherein the medical device is a robotic device, and wherein the apparatus is configured to be mounted on the robotic device.

6. The apparatus according to claim 1, wherein the sensor is a visual sensor.

7. The apparatus according to claim 1, wherein the sensor is a stationary sensor or a mobile sensor.

8. The apparatus according to claim 1 wherein the sensor is a red-green-blue (RGB) sensor, a depth sensor or an infrared sensor.

9. The apparatus according to claim 1, wherein the potential obstacle is a person and wherein the medical device includes a robotic system.

10. The apparatus according to claim 1, the processor being configured to determine the motion information of the potential obstacle comprises the processor being configured to:
    compare the first image acquired by the sensor at a time $t_{(n)}$ with the second image acquired by the sensor at a time $t_{(n-1)}$;
    calculate a movement of one or more pixels between the first image acquired at the time $t_{(n)}$ and the second image acquired at the time $t_{(n-1)}$; and
    determine the motion information of the potential obstacle based on the movement of the one or more pixels.

11. The apparatus according to claim 10, wherein the first image and the second image of the medical environment are continuous images.

12. The apparatus according to claim 11, wherein the processor is configured to estimate a moving direction and a velocity of the potential obstacle based on the movement of the one or more pixels between the first image and the second image.

13. A computer implemented method, comprising:
- detecting, in a medical environment, a potential obstacle to a medical device based on image data of the medical environment captured by a sensor;
- predicting a three-dimensional (3D) representation of the potential obstacle in the medical environment at a future point in time, wherein the 3D representation comprises a 3D point cloud, a 3D mesh or a voxel, and wherein the prediction is made by determining motion information of the potential obstacle based on a first image of the medical environment and a second image of the medical environment captured by the sensor, and predicting the 3D representation of the potential obstacle at the future point in time based at least on the determined motion information;
- predicting a 3D representation of the medical device at the future point in time;
- projecting the predicted 3D representation of the potential obstacle and the predicted 3D representation of the medical device onto at least one two-dimensional (2D) projection plane;
- determining a possibility of a collision between the potential obstacle and the medical device based on the projection;
- executing a collision avoidance action based on the determined possibility of the collision.

14. The computer implemented method according to claim 13, wherein the determined motion information of the potential obstacle includes a moving direction and a moving speed of the potential obstacle, wherein the computer implemented method further comprises determining a current state of the potential obstacle based on the first image captured by the sensor and determining a previous state of the potential obstacle based on the second image captured by the sensor, and wherein the motion information of the potential obstacle is determined based on the current state and the previous state of the potential obstacle.

15. The computer implemented method according to claim 13, wherein determining the motion information of the potential obstacle comprises:
- comparing the first image captured by the sensor at a first time with the second image captured by the sensor at a second time;
- calculating a movement of one or more pixels associated with the potential obstacle from the first image to the second image; and
- determining the motion information of the potential obstacle based on the movement of the one or more pixels associated with the potential obstacle.

16. The computer implemented method according to claim 13, wherein the 3D representation of the potential obstacle and the 3D representation of the medical device are project onto multiple 2D projection planes, and wherein
- the possibility of the collision between the potential obstacle and the medical device is determined based on a union of intersection between respective projections of the predicted 3D representation of the potential obstacle and the predicted 3D representation of the medical device on each of the multiple 2D projection planes.

17. The computer implemented method according to claim 13, wherein the medical device is a robotic device and wherein the potential obstacle is a person.

18. A computer program product comprising a non-transitory computer-readable medium having machine-readable instructions stored thereon, which when executed by a computer causes the computer to execute the method according to claim 13.

* * * * *